United States Patent
Park et al.

(10) Patent No.: US 10,182,739 B2
(45) Date of Patent: Jan. 22, 2019

(54) MAGNETIC RESONANCE IMAGING SYSTEM AND METHOD FOR GENERATING CONDUCTIVITY DISTRIBUTION IMAGE USING MAGNETIC RESONANCE ELECTRICAL IMPEDANCE TOMOGRAPHY

(71) Applicant: Korea University Research and Business Foundation, Seoul (KR)

(72) Inventors: Jaeseok Park, Seoul (KR); Hyunyeol Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 850 days.

(21) Appl. No.: 14/636,345

(22) Filed: Mar. 3, 2015

(65) Prior Publication Data
US 2015/0245784 A1  Sep. 3, 2015

(30) Foreign Application Priority Data
Mar. 3, 2014  (KR) .................. 10-2014-0024902

(51) Int. Cl.
*G01R 33/48* (2006.01)
*A61B 5/055* (2006.01)
(Continued)

(52) U.S. Cl.
CPC .......... *A61B 5/0536* (2013.01); *A61B 5/0035* (2013.01); *A61B 5/055* (2013.01);
(Continued)

(58) Field of Classification Search
USPC ................. 324/300–322; 600/407–435; 382/128–131
See application file for complete search history.

(56) References Cited

U.S. PATENT DOCUMENTS 7,259,558 B2 * 8/2007 Bieri ................ G01R 33/56358
324/306
7,439,736 B2 * 10/2008 Meaney .................. A61B 5/05
324/307

(Continued)

OTHER PUBLICATIONS

Woo, et al., "Magnetic Resonance Electrical Impedance Tomography (MREIT) for High-Resolution Conductivity Imaging", Physiological Measurement, vol. 29, No. 10, pp. R1-R26, 2008, MREIT review paper.

*Primary Examiner* — Melissa Koval
*Assistant Examiner* — Tiffany Fetzner
(74) *Attorney, Agent, or Firm* — Pearne & Gordon LLP

(57) ABSTRACT

There is provided a magnetic resonance imaging system using magnetic resonance electrical impedance tomography comprising: a current generation controller configured to control an electric current which is applied to a measurement target; a converter configured to perform analog-digital conversion of data which are obtained by a RF pulse and a gradient pulse applied to the measurement target every repetition time according to a sequence for steady state free precession (SSFP) and, also, by the applied electric current; and an image generator configured to generate an image upon a conductivity distribution of the measurement target by using output data of the converter, wherein the current generation controller controls the electric current to be applied for a preset time within a certain repetition time.

9 Claims, 8 Drawing Sheets

(51) Int. Cl.
*A61B 5/053* (2006.01)
*A61B 5/00* (2006.01)
*G01R 33/24* (2006.01)

(52) U.S. Cl.
CPC .......... *A61B 5/7203* (2013.01); *A61B 5/7221* (2013.01); *G01R 33/48* (2013.01); *A61B 2576/00* (2013.01); *G01R 33/243* (2013.01)

(56) References Cited

U.S. PATENT DOCUMENTS

| | | | | |
|---|---|---|---|---|
| 7,865,236 | B2 * | 1/2011 | Cory | A61B 5/0536 600/547 |
| 8,207,733 | B2 * | 6/2012 | Meaney | A61B 5/05 324/306 |
| 2006/0012367 | A1 * | 1/2006 | Meaney | A61B 5/05 324/315 |
| 2006/0085049 | A1 * | 4/2006 | Cory | A61B 5/0536 607/48 |
| 2006/0152219 | A1 * | 7/2006 | Bieri | G01R 33/56358 324/309 |
| 2009/0036766 | A1 * | 2/2009 | Meaney | A61B 5/05 600/410 |
| 2012/0274325 | A1 * | 11/2012 | Meaney | A61B 5/05 324/309 |
| 2014/0300354 | A1 * | 10/2014 | He | G01R 33/443 324/309 |
| 2015/0245784 | A1 * | 9/2015 | Park | A61B 5/0536 600/411 |

* cited by examiner

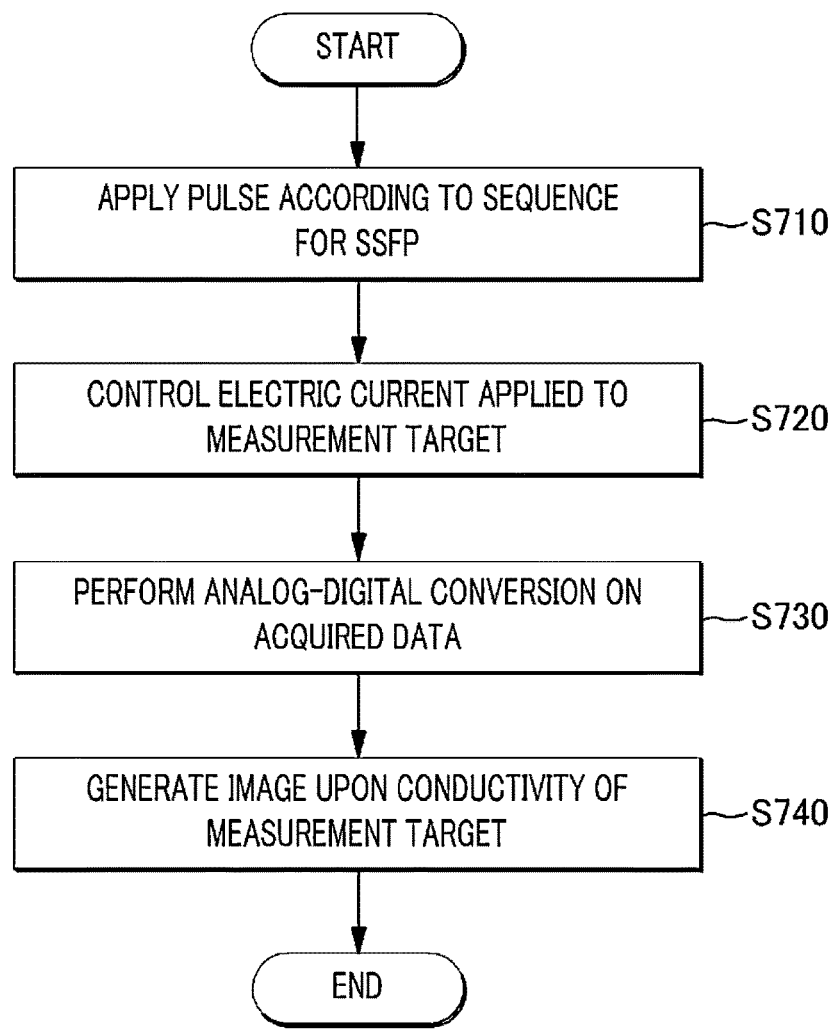

MAGNETIC RESONANCE IMAGING SYSTEM AND METHOD FOR GENERATING CONDUCTIVITY DISTRIBUTION IMAGE USING MAGNETIC RESONANCE ELECTRICAL IMPEDANCE TOMOGRAPHY

CROSS-REFERENCE TO RELATED APPLICATION

This application claims the benefit of Korean Patent Application No. 10-2014-0024902 filed on Mar. 3, 2014, the entire disclosures of which are incorporated herein by reference.

TECHNICAL FIELD

The embodiments described herein pertain generally to a magnetic resonance imaging system and a method for generating a conductivity distribution image using magnetic resonance electrical impedance tomography (MREIT).

BACKGROUND

A magnetic resonance imaging (MRI) system generates images of a human body in, e.g., transversal, longitudinal and diagonal directions. By using these MRI images, a medical state of the human body can be inspected and diagnosed.

For the purposes of accurate diagnosis, various researches are being conducted to develop a method for acquiring images having high resolution and high contrast. Among them, a research using magnetic resonance electrical impedance tomography (MREIT) is attracting attention.

MREIT is a technique of generating an in vivo conductivity distribution image by applying a magnetic resonance pulse train to a living body while inputting an electric current into the living body from an external current source. MREIT is an application of electrical impedance tomography (EIT) to an MRI apparatus. With this MREIT technique, a change in conductivity can be easily detected at any parts of the living body, and a high-resolution image can be produced.

An imaging method using a spin echo pulse train as the magnetic resonance pulse train has been widely utilized in the conventional MREIT.

In this regard, in a MREIT review paper entitled "Magnetic Resonance Electrical Impedance Tomography (MREIT) for High-Resolution Conductivity Imaging" (Woo E J et al., Physiological Measurement, vol. 29, no. 10, pp. R1-R26, 2008), MREIT is introduced and analyzed.

The conventional MREIT, however, has drawbacks in that it takes time for spin magnetization recovery, and, thus, time required to acquire data for quantitative imaging of in vivo conductivity is very long. Further, in case of the conventional MREIT, since one-to-one linear relationship is established between an electric current inputted from the outside and a phase shift of a magnetic resonance image, phase sensitivity of the image to the external electric current is limited. Thus, a large quantity of electric current needs to be applied to acquire information on an induced magnetic flux density having a high signal-to-noise ratio (SNR), which raises safety issues.

SUMMARY

In view of the foregoing problems, example embodiments provide an MRI system and a conductivity distribution image generating method, capable of generating a high-resolution image on a conductivity distribution of an inspection target by appropriately controlling an electric current to be applied while applying a sequence for steady state free precession (SSFP) to MREIT.

Further, the example embodiments also provide an MRI system and a conductivity distribution image generating method, capable of acquiring an induced magnetic flux density having a high signal-to-noise ratio (SNR) by improving phase sensitivity of an image to an external electric current through the utilization of a non-linear relationship between the electric current inputted from the outside and a SSFP image signal.

However, the problems sought to be solved by the present disclosure are not limited to the above description and other problems can be clearly understood by those skilled in the art from the following description.

In one example embodiment, there is provided a magnetic resonance imaging (MRI) system using magnetic resonance electrical impedance tomography (MREIT), the system comprising: a current generation controller configured to control an electric current which is applied to a measurement target; a converter configured to perform analog-digital conversion of data which are obtained by a RF pulse and gradient pulses applied to the measurement target every repetition time according to a sequence for steady state free precession (SSFP) and, also, by the applied electric current; and an image generator configured to generate an image upon a conductivity distribution of the measurement target by using output data of the converter, wherein the current generation controller controls the electric current to be applied for a preset time within a certain repetition time, and the preset time is determined by a time during which the RF pulse is applied and a time during which the conversion operation of the converter is performed.

Especially, the current generation controller may control the electric current to be applied for a separate time from the time during which the RF pulse is applied and the time during which the conversion operation of the converter is performed.

Especially, the current generation controller may control electric currents having opposite polarities to be applied every said repetition time.

Herein, the current generation controller may apply the electric currents alternately in synchronization with a sequence for the SSFP.

Especially, the image generator may acquire an SSFP signal model indicating information upon a magnitude and a phase of each pixel of the image by using a magnetization amount immediately before the application of the RF pulse and a magnetization amount immediately after the application of the RF pulse, and may extract information upon an induced magnetic flux density by the electric current from acquired SSFP image signals based on the SSFP signal model.

Herein, the current generation controller may control electric currents having opposite polarities to be applied alternately every said repetition time; and the image generator may acquire the SSFP signal model through a matrix operation of a Bloch equation.

Herein, the current generation controller may control electric currents having opposite polarities to be applied alternately every said repetition time; and the image generator may extract the information upon the induced magnetic flux density that minimizes a difference between a ratiometric model of the SSFP signals and a ratio between a first signal obtained when applying an electric current having a positive polarity and a second signal obtained when applying an electric current having a negative polarity.

Herein, the MRI system may further comprise an information analyzer configured to predict a signal-to-noise ratio for the extracted information upon the induced magnetic flux density information.

In another example embodiment, there is provided a method for producing a conductivity distribution image using magnetic resonance electrical impedance tomography (MREIT), the method comprising: applying an RF pulse and gradient pulses to a measurement target every repetition time according to a sequence for steady state free precession (SSFP); controlling an electric current which is applied to the measurement target such that the electric current is applied during a preset time within a certain repetition time; performing analog-digital conversion of data obtained by the RF pulse, the gradient pulses and the electric current; and generating an image upon a conductivity distribution of the measurement target by using output data obtained through the analog-digital conversion, wherein the preset time is determined by a time during which the RF pulse is applied and a time during which the conversion operation of the converter is performed.

Especially, the electric current may be controlled to be applied for a separate time from the time during which the RF pulse is applied and the time during which the conversion operation of the converter is performed.

Herein, in the controlling of the electric current, electric currents having opposite polarities may be controlled to be applied alternately every said repetition time.

Herein, in the controlling of the electric current, the electric currents may be controlled to be alternately applied in synchronization with a sequence for the SSFP.

Especially, the generating of the image may comprise: acquiring an SSFP signal model indicating information upon a magnitude and a phase of each pixel of the image by using a magnetization amount immediately before the application of the RF pulse and a magnetization amount immediately after the application of the RF pulse; and extracting information upon an induced magnetic flux density by the electric current from acquired SSFP image signals based on the SSFP signal model.

In accordance with the example embodiments, by applying the sequence for steady state free precession (SSFP), it is possible to produce a high-resolution image on a conductivity distribution at an ever higher speed.

Further, in accordance with the example embodiments, since phase sensitivity of the image to the applied electric current is increased, induced magnetic flux density information having a high signal-to-noise ratio can be acquired. Thus, the amount of the electric current that needs to be applied can be reduced.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 7 is a flowchart for describing a method for generating a conductivity distribution image in accordance with the example embodiment.

DETAILED DESCRIPTION

Figure 1:
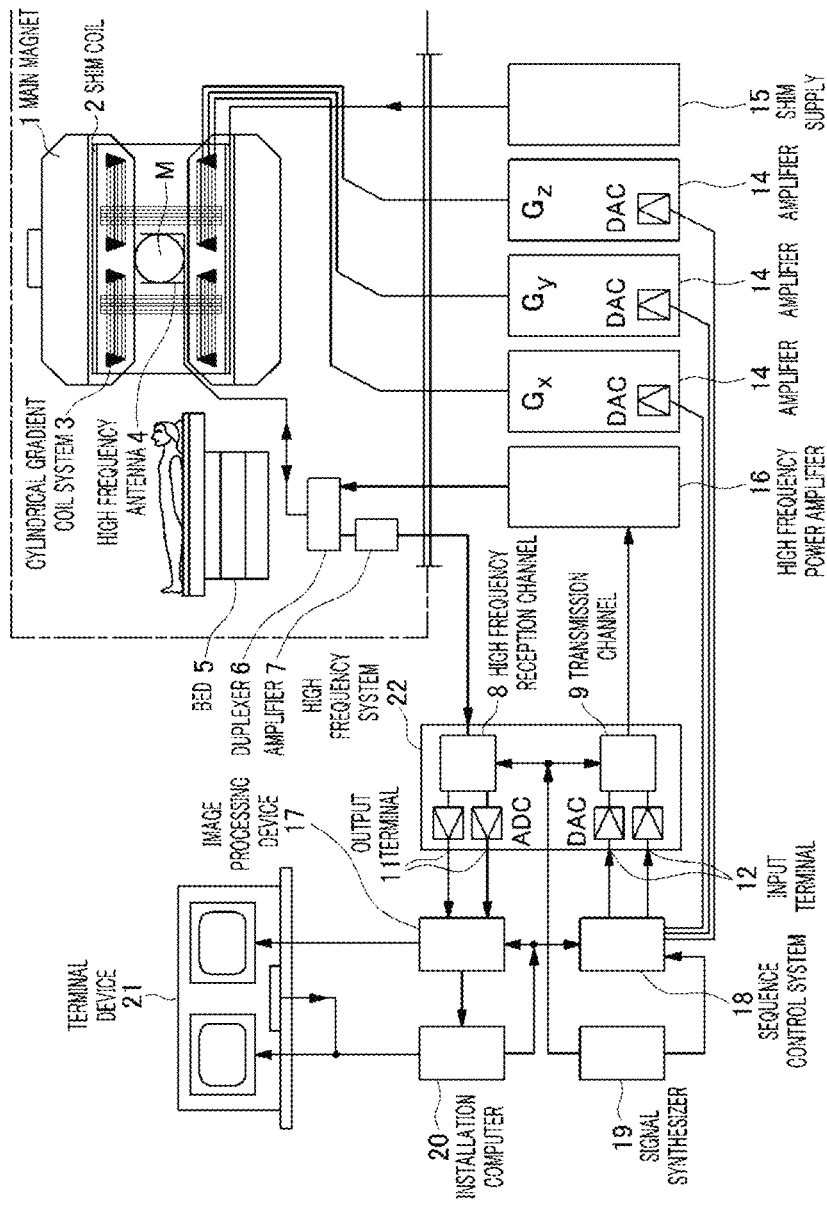
FIG. 1 is a block diagram illustrating an overall configuration of a magnetic resonance imaging system in accordance with an example embodiment.

Hereinafter, example embodiments will be described in detail so that inventive concept may be readily implemented by those skilled in the art. However, it is to be noted that the present disclosure is not limited to the illustrative embodiments and examples but can be realized in various other ways. In drawings, parts not directly relevant to the description are omitted to enhance the clarity of the drawings, and like reference numerals denote like parts through the whole document.

Through the whole document, the terms "connected to" or "coupled to" are used to designate a connection or coupling of one element to another element and include both a case where an element is "directly connected or coupled to" another element and a case where an element is "electronically connected or coupled to" another element via still another element.

Hereinafter, example embodiments will be described with reference the accompanying drawings, which form a part of the description. Here, it should be noted that the example embodiments described herein are not meant to be limiting. Other embodiments may be still conceivable by adding, modifying or deleting constituent components, without departing from the spirit or scope of the subject matter presented herein.

FIG. 1 is a block diagram illustrating an overall configuration of a magnetic resonance imaging (MRI) system in accordance with an example embodiment.

An MRI apparatus is configured to utilize a magnetic field harmless to a human body and a non-ionizing radiation (radio high frequency wave) to visualize a physical principle called nuclear magnetic resonance (NMR). The architecture of the MRI apparatus may be substantially the same as or similar to that of a conventional tomograph.

A main magnet 1 generates a strong magnetic field of a certain magnitude for polarizing or aligning nuclear spins within an inspection area of a target object such as a part of a human body to be examined. As depicted in FIG. 1, in order to measure nuclear spin resonance, the main magnet 1 generates a strong magnetic field having high homogeneity within a spherical measurement space M. A part of a human body to be examined is put into this measurement space M. At this time, to eliminate time-invariant factors while satisfying the requirement for the homogeneity, a shim plate made of a ferromagnetic material may be provided at an appropriate place. The time-invariant factors are eliminated by a shim coil 2 driven by a shim supply 15.

A cylindrical gradient coil system 3 composed of three partial windings is inserted into the main magnet 1. The partial windings generate liner gradient fields in individual directions on parallel coordinates by receiving electric currents from corresponding amplifiers 14, respectively. Here, a first partial winding of the gradient coil system 3 generates a gradient Gx in an X-direction; a second partial winding, a gradient Gy in a Y-direction; and a third partial winding, a gradient Gz in a Z-direction. Each of the amplifiers 14 is equipped with a digital-analog converter, and these digital-analog converters are controlled by a sequence control system 18 to generate a gradient pulse on exact time.

As depicted in FIG. 1, a high frequency antenna 4 is provided within the gradient coil system 3. The high frequency antenna 4 excites nuclei by converting a high frequency pulse emitted from a high frequency power amplifier 16 to an alternating filed and aligns nuclear spins within the inspection area of the target object. Further, the high frequency antenna 4 converts a nuclear spin echo signal caused by the alternating field (typically, a pulse sequence consisting of at least one high frequency pulse and at least one gradient pulse) emitted from revolving nuclear spins. At this time, the voltage converted by the high frequency antenna 4 is supplied to a high frequency reception channel 8 of a high frequency system 22 through an amplifier 7.

The high frequency system 22 includes a transmission channel 9, and the transmission channel 9 generates a high frequency pulse for exiting magnetic nuclear resonance. To elaborate, a pulse sequence is previously set by an installation computer 20, and the set pulse sequence is digitally expressed as a series of complex numbers by the high frequency system 22. These complex sequences include real parts and imaginary parts and are sent to the transmission channel 9 via digital-analog converters coupled to the high frequency system 22 after passing through input terminals 12, respectively. The transmission channel 9 then modulates the complex sequence corresponding to the pulse sequence to a high frequency carrier signal. At this time, a fundamental frequency of the high frequency carrier signal corresponds to a resonance frequency of the nuclear spins that exist within the measurement space M.

Meanwhile, for the connection between the gradient coil system 3 and the high frequency system 22, switchover from a transmitting operation by the transmission channel 9 to a receiving operation by the high frequency reception channel 8 is performed by a duplexer 6.

To elaborate, the high frequency antenna 4 radiates a high frequency pulse for exciting the nuclear spins to the inside of the measurement space M and samples echo signals representing the results. Nuclear resonance signals obtained correspondingly are decoded in the reception channel 8 of the high frequency system 22 through a phase-sensitivity mechanism, and the decoded measurement signals are converted to real parts and imaginary parts by individual analog-digital converters.

An image processing device 17 is configured to process signal data outputted from the analog-digital converters via respective output terminals 11 and reconstruct them into a single image.

The installation computer 20 is configured to manage measurement data, image data and control programs.

The sequence control system 18 generates preset individual pulse sequences according to pre-setting by a control program and controls sampling of a k-space corresponding to the individual pulse sequences. Further, the sequence control system 19 also controls gradient shift on exact time, emission of a high frequency pulse having a preset phase and a preset amplitude, and reception of a nuclear resonance signal.

A signal synthesizer 19 is configured to provide a time base for the high frequency system 22 and the sequence control system 18.

A terminal device 21 includes a keypad and one or more display units. Through this terminal device 21, an appropriate control program for generating a nuclear spin image is selected and a generated nuclear spin image is outputted.

Now, referring to FIG. 2 and FIG. 3, a detailed configuration of the MRI system using magnetic resonance electrical impedance tomography (MREIT) in accordance with the example embodiment will be discussed.

Figure 2:
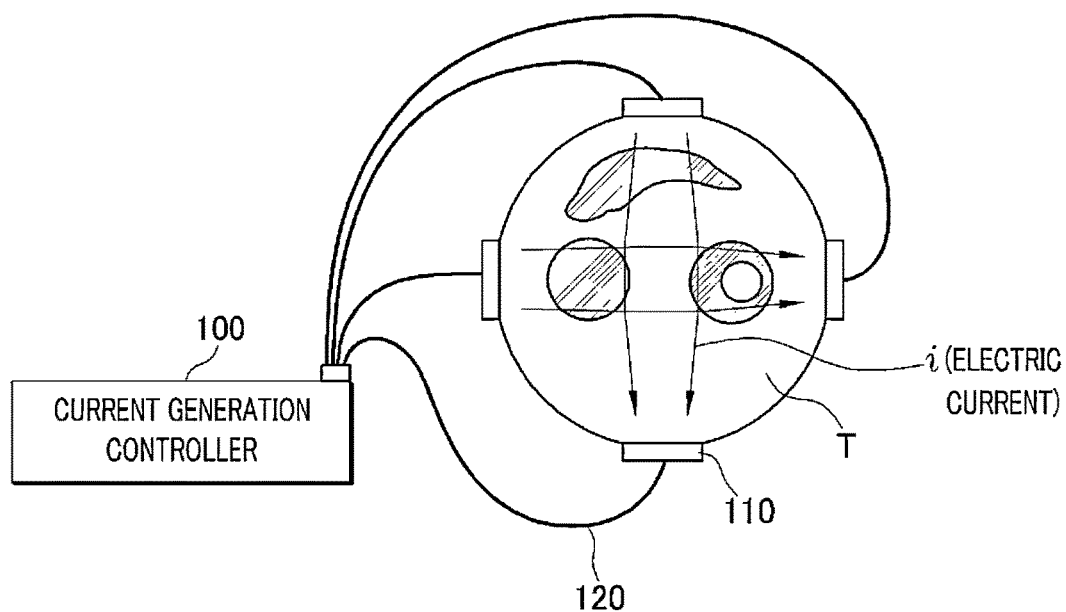
FIG. 2 is a diagram for describing a current generation controller included in the magnetic resonance imaging system in accordance with the example embodiment.
Figure 3:
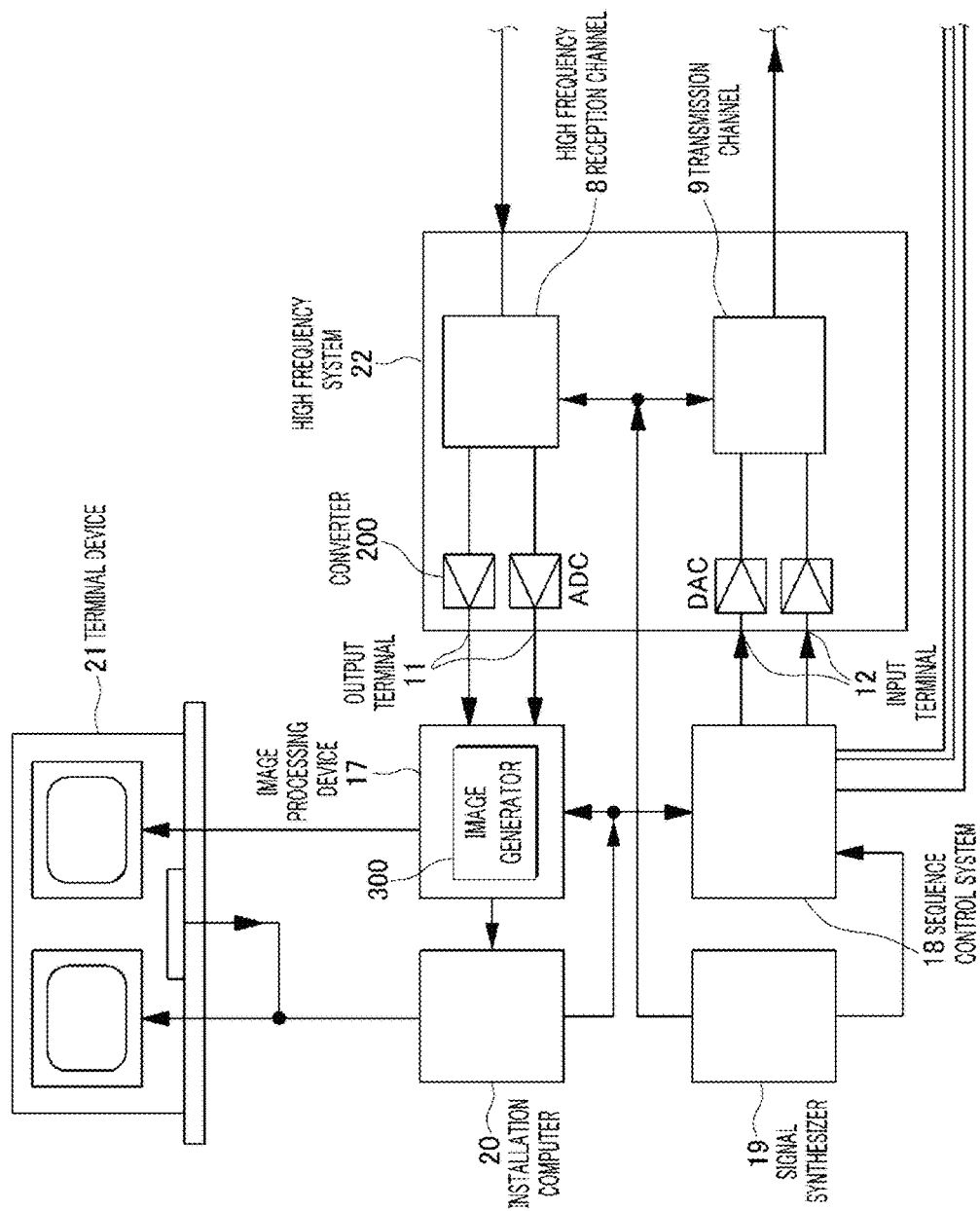
FIG. 3 is a block diagram showing an enlarged view of some components of FIG. 1.

The MRI system using the MREIT includes a current generation controller 100, a converter 200 and an image generator 300, and each of these components can be embodied as depicted in FIG. 2 and FIG. 3. However, it should be noted that the embodiment is nothing more than an example and may not be particularly limited to the shown example.

FIG. 2 is a diagram for describing the current generation controller included in the MRI system in accordance with the example embodiment.

The MRI system inputs or applies an electric current i to a measurement target T by using a MREIT technique and generates an image upon a conductivity distribution of the measurement target T through a preset processing sequence.

The current generation controller 100 generates an appropriate electric current i to be used in the MRI system and controls the electric current i that is applied to the measurement target T. One or more electrodes 110 are connected to the current generation controller 100 via respective wires 120, and each electrode 110 is located on the measurement target T and is capable of inputting an electric current to the measurement target T. Further, the current generation controller 110 may be operated in synchronization with at least a part of the components of the MRI system.

The current generation controller 100 controls the electric current to be applied for a preset time TC within a certain repetition time TR. The preset time TC may be determined by a time $t_1$ during which a RF pulse is applied and a time $t_2$ required for the converter 200 to perform a conversion operation.

Further, the current generation controller 100 also controls the magnitude of the applied electric current, and start timing and end timing for the application of the electric current to the measurement target T depending on purposes.

Detailed control operation of the current generation controller 100 will be elaborated later.

FIG. 3 is a block diagram showing an enlarged view of some components of FIG. 1.

The converter 200 is connected with the reception channel 8 of the high frequency system 22 of the MRI system. The converter 200 is implemented by an ADC and is capable of performing analog-digital conversion.

Particularly, the converter 200 performs analog-digital conversion of data which are obtained by a RF pulse and gradient pulses applied to the measurement target T every repetition time TR according to a sequence for steady state free precession (SSFP) and, also, by the applied electric current i.

Here, the sequence for SSFP may include the RF pulse and gradient pulses applied every repetition time TR. This sequence is consecutive, and a spin magnetization component within the measurement target T may reach a steady state through the consecutive sequence.

The image generator 300 generates a conductivity distribution image by quantifying a conductivity distribution of the measurement target T by using the output data of the converter 200.

Below, operations of the individual components will be discussed in further detail.

Figure 4:
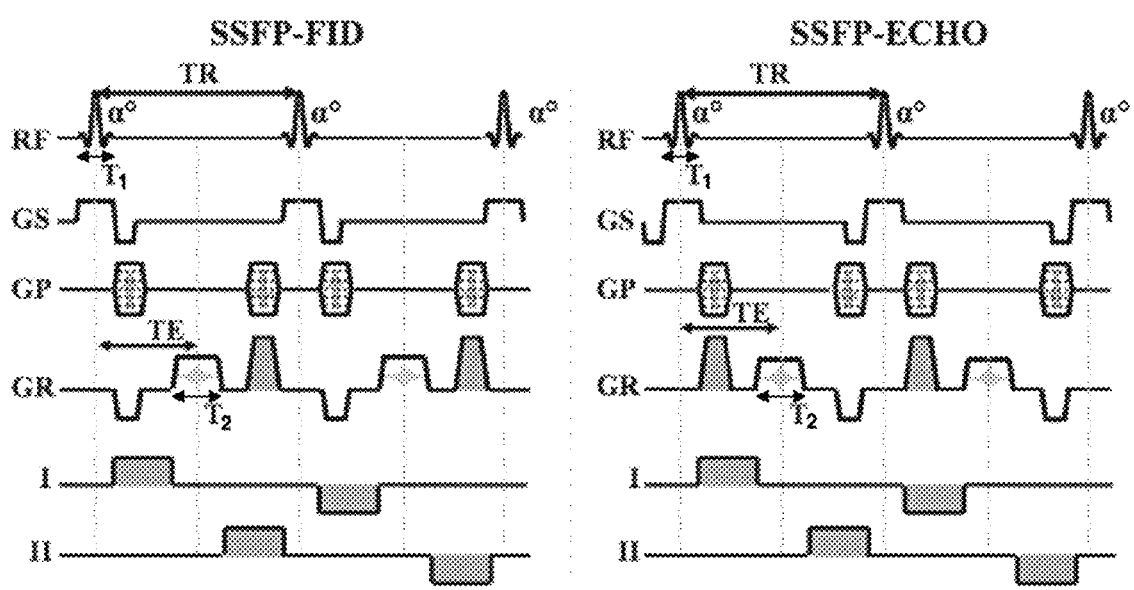
FIG. 4 is a diagram for describing a sequence for steady state free precession (SSFP) and application of an alternating current synchronized with the SSFP sequence in accordance with the example embodiment.

FIG. 4 is a diagram for describing the sequences for the SSFP and application of an alternating current in synchronization with these sequences in accordance with the example embodiment.

The sequence control system 18 of FIG. 3 is capable of generating a SSFP-FID or SSFP-ECHO pulse sequence depicted in FIG. 4 according to pre-setting by a control program.

At this time, the current generation controller 100 controls the electric current to be applied during a time separate from the time during which the RF pulse is applied and the time required for the converter 200 to perform the conversion operation. That is, the current generation controller 100 may control the time during the electric current is applied not to be overlapped with the time during which the RF power is applied and the time required for the converter 200 to perform the conversion operation.

If the RF power application time and the electric current application time are overlapped, the RF pulse may not implement an intended function, so that the image generator 300 may output an inaccurate image. Also, if the operation time of the converter 200 and the current application time are overlapped, the converter 200 may even perform analog-digital conversion of an unintended signal. Thus, it is desirable that the electric current is applied to the measurement target T within the preset repetition time TR, and this current application time can be adjusted by the current generation controller 100.

The current generation controller 100 may control electric currents I and II having opposite polarities to be applied alternately every repetition time TR, as depicted in FIG. 4. At this time, the electric currents having the opposite polarities may be applied during certain times within the repetition time TR, respectively.

As illustrated in FIG. 4, an electric current having a positive (+) polarity may be applied during a certain time every odd-numbered repetition time, and an electric current having a negative (-) polarity may be applied during a certain time every even-numbered repetition time. Alternatively, the electric currents may be applied alternately in the reverse sequence thereto.

In case of the electric current I shown in FIG. 4, the current application time within the first repetition time TR is included in a time between an RF pulse and an echo time TE. However, as in the case of the electric current II shown in FIG. 4, the electric current may be applied between a time, within the first repetition time TR, required for the converter 200 to perform the conversion operation and a time, within the next repetition time, i.e., the second repetition time TR, during which the RF pulse is applied.

That is, an alternating current such as the current I or II of FIG. 4 may be applied in correspondence to the SSFP-FID or SSFP-ECHO pulse sequence as shown in FIG. 4. Accordingly, image data can be acquired for a total number of four respective cases of SSFP-FID$_I$, SSFP-FID$_{II}$, SSFP-ECHO$_I$, and SSFP-ECHO$_{II}$.

Meanwhile, the image generator 300 is capable of acquiring an SSFP signal model indicating information upon a phase and a magnitude of each pixel of the image by using a magnetization amount immediately before the application of the RF pulse and a magnetization amount immediately after the application of the RF pulse.

To elaborate, when the current generation controller 100 controls the electric currents having the opposite polarities to be alternately applied every repetition time TR, the image generator 300 may acquire the SSFP signal model by using a matrix operation of a Bloch equation. At this time, a preset time during which each electric current is applied falls within the repetition time TR and is separate from the time during which the RF pulse is applied and the time required for the converter 200 to perform the conversion operation.

To be more specific, when the electric currents are alternately applied, the image generator 300 may perform the following processes (a) to (j).

(a) A magnetization amount ($M_{2n-1}^+$) at a time point immediately after the application of an odd-numbered (i.e., (2n−1)th) RF pulse application is expressed as a vector having x, y and z components.

(b) A magnetization dephasing by gradient pulses and a background magnetic field is expressed as the product of a longitudinal rotation matrix ($R_z$) and the vector obtained at (a).

(c) A magnetization dephasing by a positive (+) current is expressed as the product of the vertical rotation matrix ($R_z$) and a result of the process (b).

(d) A magnetization amount ($M_{2n}^-$) at a time point immediately before the application of a next RF pulse is calculated by expressing relaxations of longitudinal spin magnetization/transverse spin magnetization ($T_1/T_2$), which occur during the repetition time TR, as a matrix product and an addition, respectively.

The above-described processes (a) to (d) can be represented by the following Equation 1. Here, the matrix product is expressed as $A=\text{diag}[E_2, E_2, E_1]$, and there is establisehed a relationship of $E_{1,2}=e^{-TR/T_{1,2}}$. Further, $T_1$ denotes a longitudinal relaxation time, and $T_2$ indicates a transversal relaxation time. Further, there is established a relationship of $B=[0,0,(1-E_1)M_0]^T$. Here $M_0$ represents a magnetization amount in an equilibrium state.

$$M_{2n}^- = AR_z(\phi_b+\phi_g+\phi_c)M_{2n-1}^+ + B \qquad \text{[Equation 1]}$$

(e) An effect from an even-numbered (i.e., (2n)th) RF pulse application is expressed as the product of a transversal rotation matrix ($R_x(\alpha)$) and a result of the process (d). This operation is represented by the following Equation 2, and a denotes a flip angle.

$$M_{2n}^+ = R_x(\alpha)M_{2n}^- \qquad \text{[Equation 2]}$$

(f) The above-described processes (b) to (e) are repeated. In the process (d), a magnetization amount ($M_{2n+1}^+$) immediately after an odd-numbered (i.e., (2n−1)th) RF pulse application is calculated by the following Equation 3 in consideration of a magnetization dephasing by a negative (−) current, instead of the positive (+) current.

$$M_{2n-1}^- = AR_z(\phi_b+\phi_g-\phi_c)M_{2n}^+ + B$$

$$M_{2n+1}^+ = R_x(\alpha)M_{2n+1}^- \qquad \text{[Equation 3]}$$

(g) After equalizing the results of the processes (a) and (f), a magnetization amount immediately after an RF pulse application corresponding to an odd-numbered (i.e., (2n−1)th) repetition time is calculated through matrix inverse operation. This magnetization amount immediately after the RF pulse application corresponding to the odd-numbered (i.e., (2n−1)th) repetition time is represented by the following Equation 4.

$$M_{ss1}^+ = [I - XAZ^-XAZ^+]^{-1}X(AZ^-X+I)B \qquad \text{[Equation 4]}$$

A transverse magnetization amount immediately after the RF pulse application corresponding to the odd-numbered (i.e., (2n−1)th) repetition time can be represented by the following Equation 5

$$M_{ss1}^{xy}(0^+) = \frac{M_0(1-E_1)\sin\alpha}{D} \cdot$$
$$(A_1 e^{-j2(\phi_b+\phi_g)} + A_2 e^{-j2\phi_c} + A_3 e^{j(\phi_b+\phi_g+\phi_c)} +$$
$$A_4 e^{-j(\phi_b+\phi_g-\phi_c)} + A_5 e^{-j(\phi_b+\phi_g+\phi_c)} + A_6)$$

$$D = E_2^2(1-E_1^2)((\cos\alpha+1)^2\cos 2\phi_g + (\cos\alpha-1)^2\cos 2\phi_c) +$$
$$2E_1 E_2(1-E_2^2)(\cos 2\alpha - 1)\cos\phi_g\cos\phi_c +$$
$$2(E_1\cos\alpha+1)(E_1\cos\alpha-1) +$$
$$2E_2^4(E_1+\cos\alpha)(E_1-\cos\alpha),$$

$$A_1 = E_2^2(1+E_1)(1+\cos\alpha),$$
$$A_2 = E_2^2(1-E_1)(1-\cos\alpha),$$
$$A_3 = -E_2^2(1+E_1)(1+\cos\alpha),$$
$$A_4 = E_2(1-E_1)(1-\cos\alpha),$$
$$A_5 = 2E_2^3(E_1+\cos\alpha),$$
$$A_6 = -2(1+E_1\cos\alpha).$$

(h) Further, a transverse magnetization amount immediately after a RF pulse application corresponding to an even-numbered (i.e., (2n)th) repetition time can be represented by the following Equation 6 through the same processes as described above.

$$M_{ss2}^{xy}(0^+) = \frac{M_0(1-E_1)\sin\alpha}{D} \cdot$$
$$(A_1 e^{-j2(\phi_b+\phi_g)} + A_2 e^{j2\phi_c} + A_3 e^{j(\phi_b+\phi_g+\phi_c)} +$$
$$A_4 e^{-j(\phi_b+\phi_g+\phi_c)} + A_5 e^{-j(\phi_b+\phi_g-\phi_c)} + A_6)$$

(i) Resultantly, the signal model of alternating current-induced SSFP in each pixel of an image can be acquired by integrating the magnetization amounts calculated in the processes (g) and (h) on a cycle of 2π.

By way of example, in case of acquiring a signal through SSFP-FID$_I$ mechanism shown in FIG. 4, signals corresponding to two steady states can be represented by the following Equation 7.

$$S_{FID,ss_1} = \eta e^{j(kb+\phi_c)} \cdot \int_{-\pi}^{\pi} M_{xy,ss_1}^+(\phi_g') d\phi_g'$$
$$S_{FID,ss_2} = \eta e^{j(kb-\phi_c)} \cdot \int_{-\pi}^{\pi} M_{xy,ss_2}^+(\phi_g') d\phi_g' \quad \text{[Equation 7]}$$

Here, η denotes a signal modulation by relaxation that a tissue (measurement target) experiences between an RF pulse and an echo time (TE). Here, there is established a relationship of $\phi_g' = \phi_g + \phi_b$.

Numerical formulas for signal models of SSFP-FID$_{II}$, SSFP-ECHO$_I$ and SSFP-ECHO$_{II}$ may be developed in the similar way to that of the signal model of the above-described SSFP-FID$_I$, and, thus, detailed description thereof will be omitted here.

From acquired SSFP image signals, the image generator 300 extracts information upon an induced magnetic flux density by the applied electric currents based on the SSFP signal model described above.

To elaborate, when the current generation controller 100 controls the electric currents having the opposite polarities to be alternately applied every repetition time TR for a certain time, the image generator 300 may perform a process of minimizing a difference between a ratiometric model of the alternating SSFP signals and a ratio between a first signal and a second signal that are acquired when applying the electric currents having the positive and negative polarities, respectively, in order to extract the induced magnetic flux density information. At this time, the certain time is a separate time from the time during which the RF pulse is applied and the time required for the converter 200 to perform the conversion operation.

To be more specific, when the electric currents are alternately applied, the image generator 300 is capable of extracting the induced magnetic flux density information formed by the electric currents from acquired image signals by conducting the following processes (a) to (d) as described below.

(a) A ratio between acquired image signals $y_{odd}$ and $y_{even}$ corresponding to a positive (+) current and a negative (−) current, respectively, are calculated by the following Equation 8, and a background magnetic field signal is eliminated.

$$f(\phi_c) = y_r \text{ with } y_r = \frac{y_{odd}}{y_{even}}. \quad \text{[Equation 8]}$$

Here, $f(\phi_c)$ represents a ratio between the two the steady-state signal models defined as above.

(b) An optimization problem for searching for a $\phi_c$ value that allows a difference between the previously derived ratiometric model of the alternating SSFP signals and the acquired image signals is defined by the following Equation 9.

$$\underset{\phi_c}{\arg\min}|f(\phi_c) - y_r|^2 \quad \text{[Equation 9]}$$

(c) To regularize the value obtained at (b), other various forms of optimization problems can be defined by adding some constraints such as a total variation (TV) and the like.

As one example, an optimization problem represented by the following Equation 10 can be defined by adding a total variation (TV) and a constraint on the energy of the value obtained at (b).

$$\min\|\Phi_c\|_2^2 + \lambda TV(\Phi_c) \quad \text{[Equation 10]}$$
$$\text{s.t. } \|f(\Phi_c) - y_r\|_2 < \epsilon \text{ with}$$

$$f:\Phi_c \mapsto \begin{bmatrix} f(\phi_c(1)) \\ f(\phi_c(2)) \\ \cdots \\ \cdots \\ f(\phi_c(N_v)) \end{bmatrix}, \Phi_c = \begin{bmatrix} \phi_c(1) \\ \phi_c(2) \\ \cdots \\ \cdots \\ \phi_c(N_v) \end{bmatrix},$$

$$y_r = \begin{bmatrix} y_r(1) \\ y_r(2) \\ \cdots \\ \cdots \\ y_r(N_v) \end{bmatrix},$$

A solution of the optimization problem defined as specified above can be calculated by using various mathematical methods such as a gradient descent method.

(d) Consequently, an induced magnetic flux density $B_z$ is calculated through the following Equation 11 by using $\hat{\phi}_c(r)$ (r denotes a pixel position) which is calculated through the aforementioned optimization problem.

$$B_z(r) = \frac{\hat{\phi}_c(r)}{\gamma T_c}. \qquad \text{[Equation 11]}$$

Figure 5:
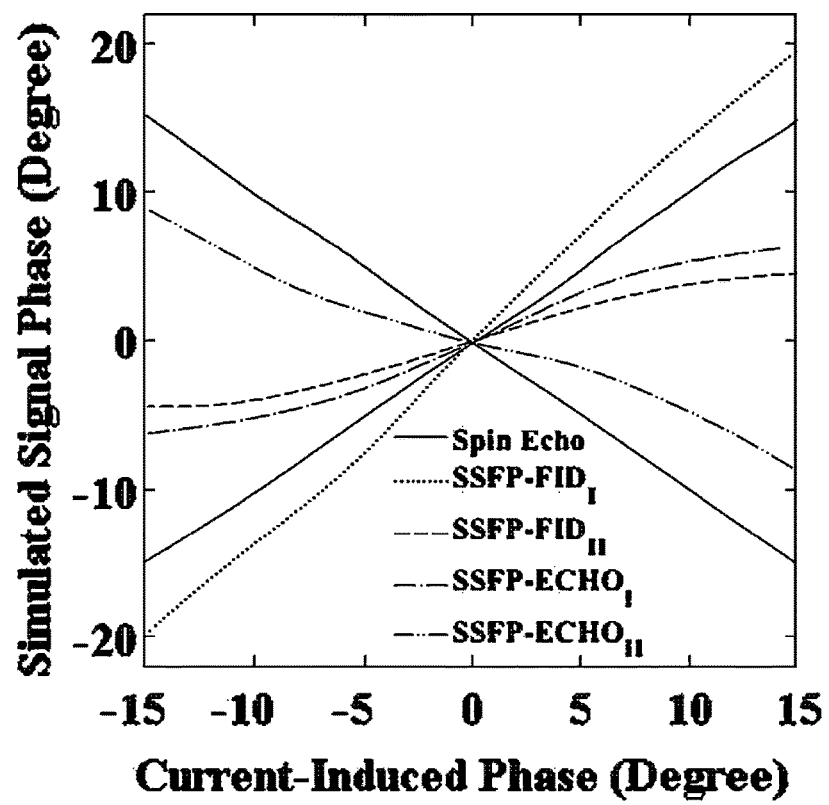
FIG. 5 is a simulation graph showing phase sensitivity according to SSFP-MREIT imaging techniques in accordance with the example embodiment.

FIG. 5 shows phase sensitivities in four cases of SSFP-MREIT imaging techniques in accordance with the example embodiment. FIG. 5 is a numerical simulation graph showing phase sensitivities according to the SSFP-MREIT imaging techniques. As depicted in FIG. 5, the imaging technique SSFP-FID$_I$ shows the highest phase sensitivity to an electric current, and this phase sensitivity value is larger than a phase sensitivity value in a conventional spin echo MREIT imaging technique.

Figure 6A:
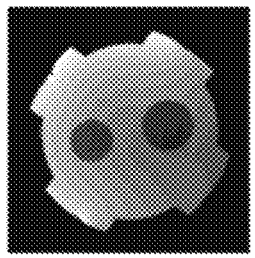
FIG. 6A is a diagram illustrating an image acquired by a conventional spin echo MREIT imaging technique.
Figure 6A:
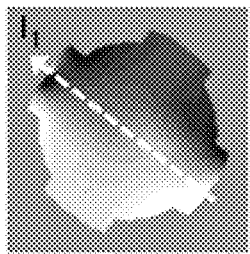
Figure 6A:
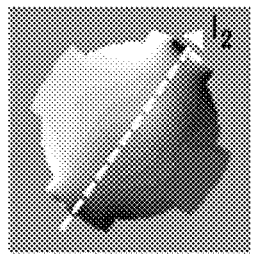
Figure 6A:
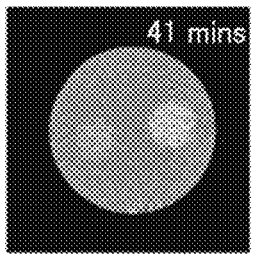

FIG. 6A is a diagram showing images acquired by the conventional spin echo MREIT imaging technique. The first image from the left of FIG. 6A is a signal intensity image; the second and third images are induced magnetic flux density images according to the application of electric currents at two orthogonal directions; and the fourth image is a restored conductivity distribution image.

Figure 6B:
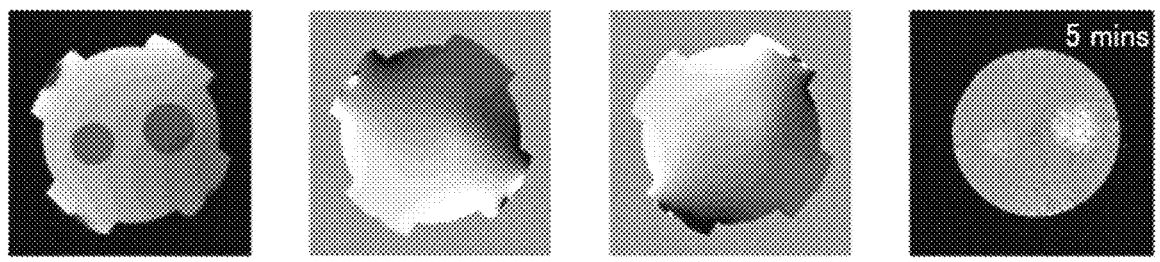
FIG. 6B is a diagram illustrating an image acquired by the magnetic resonance imaging system in accordance with the example embodiment.

FIG. 6B is a diagram showing images acquired by the SSFP-FID$_I$ imaging technique in accordance with the example embodiment. The first image from the left of FIG. 6B is a signal intensity image; the second and third images are induced magnetic flux density images according to the application of electric currents at two orthogonal directions; and the fourth image is a restored conductivity distribution image.

As can be seen from these figures, in accordance with the example embodiment, it is possible to acquire a conductivity distribution image having a quality similar to that of a conductivity distribution image obtained by the conventional spin echo MREIT technique within an even shorter image acquisition time. That is, with the convention spin echo MREIT imaging technique as depicted in FIG. 6A, it takes 41 minutes to acquire the conductivity distribution image, whereas it is possible to acquire the conductivity distribution image having the similar quality in only 5 minutes in the SSFP-FID$_I$ technique in accordance with the example embodiment. That is, by applying the SSFP sequence in accordance with the example embodiment, magnetic resonance electrical impedance image data can be obtained at a high speed.

Additionally, an MRI system using MREIT in accordance with another example embodiment may further include an information analyzer (not shown) in addition to the components as described above.

The information analyzer (not shown) is connected with some components within the MRI system and predicts a signal-to-noise ratio (SNR) for induced magnetic flux density information extracted based on an SSFP signal model described above. The information analyzer is capable of predicting the SNR for the induced magnetic flux density information through the following Equation 12.

$$\sigma_{B_z}, SSFP = \frac{1}{\sqrt{2}\,\gamma T_c \Upsilon_M h'(\overline{\phi}_c)}. \qquad \text{[Equation 12]}$$

Here, $\sigma_{B_z}$,SSFP represents a standard deviation of the induced magnetic flux density information; $\gamma$, a gyromagnetic ratio; $T_c$, a current application time; and a $\Gamma_M$, a SNR of a signal intensity image. Further, $h'(\overline{\phi}_c)$ means a first derivative of a relation function between the induced magnetic flux density information and the phase of the acquired image, i.e., phase sensitivity of the image.

As can be seen from the Equation 12, with the rise of the phase sensitivity of the acquired image, the SNR of the induced magnetic flux density improves. That is, by applying external electric currents alternately in synchronization with the SSFP sequence as in the example embodiment, the SNR of the induced magnetic flux density can be improved.

Accordingly, even when the SSFP sequence is applied to the MREIT, an SNR of induced magnetic flux density can be predicted, so that user convenience can be improved.

Now, a method for producing a conductivity distribution image using MREIT in accordance with an example embodiment will be explained with reference to FIG. 7.

FIG. 7 is a flowchart for describing the method of producing a conductivity distribution image in accordance with the example embodiment. Here, the above-described MRI system may be used to implement this method.

First, the MRI system applies a RF pulse and gradient pulses every repetition time TR to a measurement target T according to a steady-state free precession (SSFP) sequence (S710).

Further, the MRI system controls an electric current i applied to the measurement target T such that the electric current i is applied for a preset time within the repetition time TR (S720).

At this time, the preset time may be determined depending on a time during which the RF pulse is applied and a time required for the converter to perform a conversion operation.

To elaborate, the MRI system may control the electric current to be applied during a time period separate from the time during which the RF pulse is applied and the time required for the converter to perform the conversion operation.

At this time, the MRI system may control electric currents having opposite polarities to be alternately applied every repetition time TR for the preset time within the repetition time TR.

Subsequently, the MRI system performs analog-digital conversion upon data acquired by the RF pulse, the gradient pulses and the electric currents (S730).

Then, the MRI system produces an image showing a conductivity distribution of the measurement target T by using output data obtained at S730 (conversion process) (S740).

To elaborate, an SSFP signal model indicating information upon a magnitude and a phase of each pixel of an image can be acquired by using a magnetization amount immediately before the RF pulse application and a magnetization amount immediately after the RF pulse application.

From acquired SSFP image signals, information upon induced magnetic flux density resulting from the applied electric currents based on the SSFP signal model.

With the above-described method for producing a conductivity distribution image in accordance with the example embodiment, it is possible to produce a high-resolution image upon a conductivity distribution at an ever higher speed by using the SSFP sequence. Further, by improving phase sensitivity of the image to the applied electric currents, induced magnetic flux density information having high signal-noise ratio can be obtained, so that the amount of the electric currents that need to be applied can be reduced.

The above description of the illustrative embodiments is provided for the purpose of illustration, and it would be understood by those skilled in the art that various changes and modifications may be made without changing technical conception and essential features of the illustrative embodiments. Thus, it is clear that the above-described illustrative embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

We claim:

1. A magnetic resonance imaging (MRI) system using magnetic resonance electrical impedance tomography (MREIT), the MRI system comprising:
   a current generation controller configured to control an electric current which is applied to a measurement target;
   a converter configured to perform an analog-digital conversion of data which are obtained by an RF pulse and gradient pulses which are applied to the measurement target every repetition time according to a sequence performing steady state free precession (SSFP) and, also, by the applied electric current; and
   an image generator configured to generate an MREIT image from a conductivity distribution of the measurement target by using output data obtained from the converter,
   wherein the current generation controller controls the electric current that is applied for a preset time interval within a certain repetition time, the preset time interval is determined by a time interval during which the RF pulse is applied and a time interval during which the analog-digital conversion operation of the converter is performed,
   the current generation controller controls the electric current being applied over a separate time interval from the time interval during which the RF pulse is applied and the time interval during which the analog-digital conversion operation of the converter is performed, and
   the image generator acquires an SSFP signal model containing magnitude and phase information with respect to each pixel of the generated MREIT image by using a magnetization amount immediately before the application of the RF pulse and a magnetization amount immediately after the application of the RF pulse, and subsequently extracts an induced magnetic flux density of the applied electric current from the acquired SSFP image signals using the SSFP signal model.

2. The MRI system of claim 1, wherein the current generation controller controls electric currents having opposite polarities that are applied alternately every said repetition time; and
   the image generator extracts the induced magnetic flux density that minimizes a difference between a ratiometric model of the SSFP signals and a ratio between a first signal that is obtained when applying an electric current having a positive polarity and a second signal that is obtained when applying an electric current having a negative polarity.

3. The MRI system of claim 1, wherein the current generation controller controls electric currents having opposite polarities which are applied every said repetition time.

4. The MRI system of claim 3, wherein the current generation controller applies the electric currents alternately in synchronization with a sequence that performs the SSFP imaging sequence.

5. The MRI system of claim 1, further comprising:
   an information analyzer configured to predict a signal-to-noise ratio of the extracted induced magnetic flux density information.

6. The MRI system of claim 1 wherein the current generation controller controls electric currents having opposite polarities that are applied alternately every said repetition time; and
   the image generator acquires the SSFP signal model by the application of a matrix operation on a Bloch equation.

7. A method of producing a conductivity distribution image using magnetic resonance electrical impedance tomography (MREIT), the method comprising:
   applying an RF pulse and gradient pulses to a measurement target every repetition time according to a sequence that performs steady state free precession (SSFP);
   controlling an electric current which is being applied to the measurement target such that the electric current is applied during a preset time interval within a certain repetition time;
   performing analog-digital conversion of data obtained by the RF pulse, the gradient pulses and the electric current; and
   generating an MREIT image from a conductivity distribution of the measurement target by using output data obtained through the analog-digital conversion,
   wherein the preset time interval is determined by a time interval during which the RF pulse is applied and a time interval during which the analog-digital conversion operation of the converter is performed, and
   wherein the electric current is controlled to be applied for a separate time interval from the time interval during which the RF pulse is applied and the time interval during which the analog-digital conversion operation of the converter is performed, and
   wherein the generating of the MREIT image comprises:
       acquiring an SSFP signal model containing magnitude and phase information with respect to each pixel of the generated MREIT image by using a magnetization amount immediately before the application of the RF pulse and a magnetization amount immediately after the application of the RF pulse; and
       extracting an induced magnetic flux density of the applied electric current from the acquired SSFP image signals using the SSFP signal model.

8. The method of claim 7, wherein in the controlling of the electric current, electric currents having opposite polarities are controlled and applied alternately every said repetition time.

9. The method of claim 8, wherein in the controlling of the electric current, the electric currents are controlled and alternately applied in synchronization with the sequence that performs the SSFP.

* * * * *

UNITED STATES PATENT AND TRADEMARK OFFICE
CERTIFICATE OF CORRECTION

PATENT NO. : 10,182,739 B2
APPLICATION NO. : 14/636345
DATED : January 22, 2019
INVENTOR(S) : Jaeseok Park et al.

Page 1 of 1

It is certified that error appears in the above-identified patent and that said Letters Patent is hereby corrected as shown below:

In the Specification

Column 8, Line 68, after [Equation 4], please insert -- where $X = R_x(\alpha)$, $Z^+ = R_z(\phi_b + \phi_g + \phi_c)$, and $Z^- = R_z(\phi_b + \phi_g - \phi_c)$ --.

Column 9, Line 21, "$A_3 = -E_2^2(1 + E_1)(1 + \cos\alpha)$," should be -- $A_3 = -E_2(1 + E_1)(1 + \cos\alpha)$, --.

Signed and Sealed this
Thirtieth Day of April, 2019

Andrei Iancu
*Director of the United States Patent and Trademark Office*